US012611259B2

(12) United States Patent
Huemmer et al.

(10) Patent No.: US 12,611,259 B2
(45) Date of Patent: Apr. 28, 2026

(54) DETERMINING HOW WELL AN OBJECT INSERTED INTO A PATIENT'S BODY IS POSITIONED

(71) Applicant: Siemens Healthineers AG, Forchheim (DE)

(72) Inventors: Christian Huemmer, Lichtenfels (DE); Andreas Fieselmann, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 1195 days.

(21) Appl. No.: 17/480,242

(22) Filed: Sep. 21, 2021

(65) Prior Publication Data

US 2022/0096167 A1 Mar. 31, 2022

(30) Foreign Application Priority Data

Sep. 25, 2020 (DE) ..................... 10 2020 212 086.2

(51) Int. Cl.
　　*A61B 34/20* (2016.01)
　　*G06T 7/00* (2017.01)

(52) U.S. Cl.
　　CPC ............ *A61B 34/20* (2016.02); *G06T 7/0012* (2013.01); *A61B 2034/2065* (2016.02); (Continued)

(58) Field of Classification Search
　　CPC ........ A61B 34/20–30; A61B 90/37–39; A61B 6/487; A61B 2090/374–378; (Continued)

(56) References Cited

U.S. PATENT DOCUMENTS 10,022,192 B1 7/2018 Ummalaneni
2003/0187358 A1 10/2003 Okerlund et al.
(Continued)

FOREIGN PATENT DOCUMENTS

CN 1503184 A 6/2004
CN 1748646 A 3/2006
(Continued)

OTHER PUBLICATIONS

Wu et al. (2011), "Learning-based hypothesis fusion for robust catheter tracking in 2D X-ray fluoroscopy", https://doi.org/10.1109/ CVPR.2011.5995553, Status: Jul. 24, 2020.
(Continued)

*Primary Examiner* — Carolyn A Pehlke
(74) *Attorney, Agent, or Firm* — Harness, Dickey & Pierce, P.L.C.

(57) ABSTRACT

A method is for determining a positioning quality of an external apparatus inserted into a patient's body. In the method, image data of the patient's body is detected; an at least one first anatomical landmark is detected in or with a first subregion, in which the external apparatus is positioned as expected; at least a first subsection of the external apparatus is sought in or with the at least one first subregion; a second anatomical landmark is detected in or with at least one second subregion; at least one second subsection is then detected based upon the already localized subsection; and a quality of the positioning of the at least one second subsection is determined by measuring a suitable dimension between the localized at least one second subsection and the at least one second landmark. A training method, a positioning quality determination facility and a training facility are also disclosed.

19 Claims, 5 Drawing Sheets

(52) U.S. Cl.
CPC .............. *G06T 2207/20081* (2013.01); *G06T 2207/20084* (2013.01); *G06T 2207/20101* (2013.01); *G06T 2207/30012* (2013.01)

(58) Field of Classification Search
CPC ...... A61B 2090/3966; A61B 34/00–20; G06T 7/0012
See application file for complete search history.

(56) References Cited

U.S. PATENT DOCUMENTS

| | | | |
|---|---|---|---|
| 2006/0253032 A1 | 11/2006 | Altmann et al. | |
| 2008/0139930 A1 | 6/2008 | Weese et al. | |
| 2011/0085706 A1 | 4/2011 | Villain et al. | |
| 2013/0072788 A1 | 3/2013 | Wu et al. | |
| 2015/0209113 A1 | 7/2015 | Burkholz et al. | |
| 2016/0120522 A1* | 5/2016 | Weingarten | A61B 6/487 |
| | | | 378/42 |
| 2017/0143235 A1 | 5/2017 | Besz et al. | |
| 2017/0330319 A1 | 11/2017 | Xu et al. | |
| 2018/0005083 A1 | 1/2018 | Georgescu et al. | |
| 2018/0085079 A1 | 3/2018 | Krimsky | |
| 2018/0158209 A1 | 6/2018 | Fine et al. | |
| 2018/0366035 A1 | 12/2018 | Dunbar et al. | |
| 2019/0069955 A1 | 3/2019 | Popovic et al. | |
| 2019/0183586 A1 | 6/2019 | Rotilio et al. | |
| 2019/0239961 A1* | 8/2019 | Birenbaum | A61B 6/466 |
| 2019/0355149 A1 | 11/2019 | Avendi et al. | |
| 2020/0196908 A1 | 6/2020 | Ben-Haim et al. | |
| 2020/0242767 A1* | 7/2020 | Zhao | G06T 7/344 |
| 2020/0258216 A1 | 8/2020 | Sharma et al. | |
| 2021/0068772 A1* | 3/2021 | Weingarten | A61B 6/486 |

FOREIGN PATENT DOCUMENTS

| | | | |
|---|---|---|---|
| CN | 1853573 | A | 11/2006 |
| CN | 101111193 | A | 1/2008 |
| CN | 102077248 | A | 5/2011 |
| CN | 106061386 | A | 10/2016 |
| CN | 107865692 | A | 4/2018 |
| CN | 108601628 | A | 9/2018 |
| CN | 109069207 | A | 12/2018 |
| CN | 109074665 | A | 12/2018 |
| CN | 110831537 | A | 2/2020 |
| CN | 111563496 | A | 8/2020 |
| DE | 102008020657 | A1 | 11/2009 |
| WO | WO 2007066096 | A2 | 6/2007 |
| WO | WO 2019209767 | A1 | 10/2019 |

OTHER PUBLICATIONS

Lee et al. (2017), "A Deep-Learning System for Fully-Automated Peripherally Inserted Central Catheter (PICC) Tip Detection", https://dx.doi.org/10.1007/s10278-017-0025-z.

Yi et al. (2020), "Computer-Aided Assessment of Catheters and Tubes on Radiographs—How Good is Artificial Intelligence for Assessment?", https://arxiv.org/abs/2002.03413 Stand: Jul. 24, 2020.

Yi et al. (2018), "Automatic Catheter and Tube Detection in Pediatric X-ray Images Using a Scale-Recurrent Network and Synthetic Data", https://arxiv.org/pdf/1806.00921.pdf Stand: Jul. 24, 2020.

Pikwer et al. (2008),"The incidence and risk of central venous catheter malpositioning: a prospective cohort study in 1619 patients", https://www.ncbi.nlm.nih.gov/pubmed/18326129 Stand: Jul. 24, 2020.

Leitsmann, Jessica: "Evaluation der Lage zentralvenöser Katheter bei spontan atmenden Patienten"; Dissertation an der Friedrich-Schiller-Universität Jena; Veröffentlichungsdatum: Jun. 15, 2012; URL: https://www.db-thueringen.de/receive/dbt mods 00020559.

Lakhani (2017), "Deep Convolutional Neural Networks for Endotracheal Tube Position and X-ray Image Classification: Challenges and Opportunities", https://dx.doi.org/10.1007/s10278-017-9980-7.

Tsotsolis et al. (2015), "Pneumothorax as a complication of central venous catheter insertion", http://dx.doi.org/10.3978/j.issn.2305-5839.2015.02.11 Stand: Jul. 24, 2020.

Raut et al. (2015), "Malposition of a nasogastric tube", https://dx.doi.org/10.4103%2F0971-9784.154502.

healthcare-in-europe.com (Nov. 25, 2018), "Deep learning software helps to locate the carina", https://healthcare-in-europe.com/en/news/deep-learning-software-helps-to-locate-the-carina.html (accessed Sep. 24, 2019).

Lee et al. (2017), "Machine Intelligence for Accurate X-ray Screening and Read-out Priorization: PICC Line Detection Study", https://siim.org/resource/resmgr/siim2017/presentations/siim17_analytics_deep1-lee.pdf (accessed Sep. 24, 2019).

GE (Mar. 16, 2018), "Healthcare Denmark visit to UCSF The UCSF/GE partnership on Artificial Intelligence". https://www.himss.eu/sites/himsseu/files/community/community_presentations/HIMSS18-Danish/GE%20-%20UCSF.pdf (accessed Sep. 24, 2019).

German Office Action mailed May 25, 2021.

* cited by examiner

300

400

DETERMINING HOW WELL AN OBJECT INSERTED INTO A PATIENT'S BODY IS POSITIONED

PRIORITY STATEMENT

The present application hereby claims priority under 35 U.S.C. § 119 to German patent application number DE102020212086.2 filed Sep. 25, 2020, the entire contents of which are hereby incorporated herein by reference.

FIELD

Example embodiments of the invention generally relate to a method for determining a positioning quality of an external apparatus inserted into a patient's body. Furthermore, example embodiments of the invention relates to a method for providing a trained function. Moreover, example embodiments of the invention relates to a positioning quality determination facility. Furthermore, example embodiments of the invention relates to a training facility. Furthermore, example embodiments of the invention also relates to a medical imaging facility.

BACKGROUND

With the medical treatment and care of patients, external apparatuses are frequently inserted into the body of the patient. One clear example is a patient who is treated in intensive care and who is supplied with vital substances by way of a plurality of tubes and the vital functions of whom are monitored with the aid of a plurality of measuring probes inserted into the body.

Specific examples of apparatuses inserted into the body are:

a central vein catheter, which is inserted into a patient's body by way of a vein, a peripherally inserted central catheter, which is inserted into a patient's body by way of an arm vein, an endotracheal probe, which is inserted by way of the mouth and the trachea, a nasogastric probe, which is inserted by way of the nose.

If such an invasive apparatus is incorrectly positioned in the body, it may result in life-threatening complications. The incorrect positioning of central venous catheters may result, for instance, in infections, thromboses, occlusions or a pneumothorax, i.e. accumulations of air in the pleura or the pleural space between the two pleural layers. An incorrectly positioned peripherally inserted central catheter can result in a thrombus formation or arrhythmia. An incorrectly inserted endotracheal probe may result in hyperinflation, i.e. an excessive inflation of the lungs, a pneumothorax, an atelectasis, i.e. a ventilation deficiency of the lungs or a hypoxemia, i.e. a lower oxygen content in the arterial blood of the contralateral non-ventilated lung. An incorrectly positioned nasogastric probe may result in a pneumothorax, a pleural effusion, a retropharyngeal abscess, or a lung abscess.

Furthermore, an incorrectly positioned external apparatus is not able to fulfil its intended purpose.

In order to avoid an incorrect positioning of an external apparatus in the human body, medical images are typically produced and the position of the apparatus in the body of a patient is monitored by a radiologist. These images are recorded after the initial placement and can be recorded regularly to ensure that the apparatus is still at the correct position if, for instance, the apparatus is to remain in the patient for a longer period of time, such as, for instance, in the case of a central venous catheter.

With this procedure, problems nevertheless occur in that the evaluation of the medical images by a radiologist, in order to determine the position of the external apparatus, is often carried out with a delay and not immediately after the image recording. If an external apparatus is left incorrectly positioned undiscovered for too long, this instance may result in serious complications for the patient.

The interpretation of the medical image, in order to determine the position of an external apparatus, is subjective and depends upon the experience of the specialist who is carrying out this examination.

SUMMARY

Approaches exist of automatically identifying external apparatuses in image data records by using artificial intelligence. However, the inventors have discovered that the problem here is that large quantities of data have to be processed in order to find and classify objects in the images. Moreover, there is often the difficulty of correctly classifying objects detected in the images.

Embodiments of the invention are directed to a method and an apparatus for automatically finding external apparatuses in the body of a patient with improved reliability and less data processing effort.

Embodiments of the invention are directed to a method for determining a positioning quality of an external apparatus inserted into a patient's body, a method for providing a trained function, a positioning quality determination facility, a training facility and a medical imaging facility.

With at least one embodiment of the inventive method for determining a positioning quality of an external apparatus inserted into a patient's body, image data is detected from the patient's body. This image data comprises information relating to the inside of a patient. In particular, the external apparatus in the inside of the body of the patient is also mapped onto the image data. An apparatus inserted into the body of a patient by way of a body opening or a vessel or an artificially created opening is to be understood to mean an external apparatus. Furthermore, one or more first anatomical landmarks are detected in or with a first subregion, in which the apparatus is positioned as expected.

With at least one embodiment of the inventive method for providing a trained function, input training data is received, which comprises medical image data of test persons of a training database. This method is suited in particular to the case in that the identification and localization of the landmarks and/or the subsections of the apparatus is to take place by applying artificial intelligence or in an AI-based manner. In order to realize such an approach, a function is trained by applying a machine learning, for instance realized by an artificial neural network. To this end, output training data, which is assigned to the input training data, is received in addition to the input training data. Here the output training data comprises landmarks which are assigned to a first and a second section of an external apparatus inserted into a patient's body, as well as data for identifying and localizing the first and second section of the apparatus inserted into a patient's body. Furthermore, a function is trained via an algorithm based on machine learning based upon the input data and the output data. Advantageously, no complex model approach for determining the function needs to be laboriously designed, but the function is instead produced automatically based upon the available database of training data. In particular, with a large number of different parameters to be taken into account or a phenomenon which cannot be detected adequately by a model, one such procedure will outclass the purely model-based approach.

At least one embodiment of the inventive positioning quality determination facility has an input interface for detecting image data from a patient's body. At least one embodiment of the inventive positioning quality determination facility also comprises a landmark detection unit for AI-based detection of first anatomical landmarks in or with at least one first subregion, in which an external apparatus is positioned as expected. At least one embodiment of the inventive positioning quality determination facility also comprises an identification unit for preferably AI-based searching and localizing of at least one subsection of the external apparatus in or with the at least one first subregion. Here the landmark detection unit is designed, in the case that the external apparatus has been detected in or with the first subregion, to identify and localize at least one second landmark in or with at least one second subregion, through which at least one second section of the external apparatus runs as expected and which comprises a clinically relevant region. The identification unit is furthermore designed to localize the external apparatus in or with the at least one second subregion based upon the already localized subsection of the external apparatus. The positioning quality determination facility comprises a quality determination unit for determining a quality of the positioning of the second subsection of the external apparatus by measuring a physical dimension, for instance a gap or angle between the localized external apparatus and the at least one second landmark.

At least one embodiment of the inventive training facility has a first training interface for receiving input training data, which comprises medical image data of test persons of a training database. At least one embodiment of the inventive training facility also comprises a second training interface for receiving output training data, which is assigned to the input training data. Here the output training data comprises landmarks, which mark a previously known position of a first subsection and a desired position or a position, to be checked, of a second subsection of an apparatus inserted into a patient's body, as well as data for identifying and localizing the first and second subsection of the apparatus inserted into a patient's body. Part of at least one embodiment of the inventive training facility is also a training unit for training a function based upon the training input data and the training output data and an output interface for outputting the trained function. The inventive training facility shares the advantages of the inventive training method.

At least one embodiment of the inventive imaging medical facility has the positioning quality determination facility and the inventive training facility. At least one embodiment of the inventive imaging medical facility combines the advantages of at least one embodiment of the inventive positioning quality determination facility and at least one embodiment of the inventive training facility.

Essentially these components can however also be realized to some extent, particularly if it involves particularly rapid calculations, in the form of software-assisted hardware, for instance FPGAs or suchlike. Similarly the required interfaces, for instance when it only involves a takeover of data from other software components, can be embodied as software interfaces. They can also be configured as interfaces constructed from hardware, which are controlled by suitable software.

A realization largely through software has the advantage that even medical imaging facilities which have previously been used can be easily set up by a software update to operate in the inventive manner, possibly by retrofitting the requisite hardware. In this respect, the object is also achieved by a corresponding computer program product with a computer program which can be loaded directly into a storage facility of a medical imaging facility and comprises program portions in order to carry out all the steps of the inventive method when the computer program is executed in the medical imaging facility.

Such a computer program product can comprise, where relevant, in addition to the computer program, further constituents, such as, for example, documentation and/or additional components including hardware components, for example, hardware keys (dongles, etc.) in order to use the software.

By way of a software implementation, the methods can be carried out in a reproducible and less error-prone manner on different medical imaging facilities.

For transport to the storage facility of the medical imaging facility and/or for storage at the medical imaging facility, a computer-readable medium, for example, a memory stick, a hard disk or another transportable or permanently installed data carrier can be used, on which the program portions of the computer program which can be read in and executed by a data processing facility, for instance a computer unit, are stored. For this purpose, the computer unit can have, for example, one or more cooperating microprocessors or the like.

At least one embodiment of the inventive application is directed to a method for determining a positioning quality of an apparatus inserted into a body of a patient, the method comprising:

detecting image data, of the body of the patient, representing the apparatus inside the body of the patient;

detecting at least a first anatomical landmark, in or with at least one first subregion, upon the apparatus being positioned as expected;

searching for at least one first subsection of the apparatus in or with the at least one first subregion, upon the apparatus being detected and localized;

detecting at least one second anatomical landmark, in or with at least one second subregion, by which the apparatus proceeds as expected and including a clinically relevant region;

detecting and localizing at least one second subsection of the apparatus in or with the at least one second subregion, based upon the at least one first subsection of the apparatus previously localized, to determine a localized at least one second subsection of the apparatus; and determining a quality of positioning of the at least one second subsection of the apparatus by measuring a suitable dimension between the localized at least one second subsection of the apparatus detected, and the at least one second landmark detected.

At least one embodiment of the inventive application is directed to a method for providing a trained function, comprising:

receiving input training data including image data of test persons of a training database;

receiving output training data assigned to the input training data, the output training data including landmarks assigned to at least one first section of an apparatus inserted into a body of a patient and at least one second section of the apparatus inserted into the body of the patient, and data for identifying and localizing the at least one first section of the apparatus inserted into the body of the patient and second section of the apparatus inserted into the body of the patient; and training a function, via an algorithm based on machine learning, based upon the input training data received and the output training data received.

At least one embodiment of the inventive application is directed to a positioning quality determination facility, comprising:

an input interface to detect image data from a body of a patient, representing an apparatus inside of the body of the patient;

a landmark detection unit to detect at first anatomical landmarks in or with at least one first subregion, in which the apparatus is positioned as expected, an identification unit to search for and localize at least one first subsection of the apparatus in or with the at least one first subregion, wherein the landmark detection unit is designed, upon the apparatus being detected in or with the at least one first subregion, to detect at least one second landmark in or with at least one second subregion, through which the apparatus proceeds as expected, and which includes a clinically relevant region, and the identification unit is designed to localize the apparatus in or with the at least one second subregion based upon the at least one first subsection of the apparatus previously localized, to determine a localized at least one second subsection of the apparatus; and a quality determination unit to determine a quality of positioning of the at least one second subsection of the apparatus by measuring a suitable dimension between the localized at least one second subsection of the apparatus detected and the at least one second landmark detected.

At least one embodiment of the inventive application is directed to a training facility, comprising:

a first training interface to receive input training data including image data of test persons of a training database;

a second training interface to receive output training data, assigned to the input training data, the output training data including landmarks assigned to at least one first subsection of an apparatus insertable into a body of a patient and an at least one second subsection of the apparatus insertable into the body of the patient, and including data for identifying and localizing the at least one first subsection of the apparatus insertable into the body of the patient and second subsection of the apparatus insertable into the body of the patient;

a training unit to train a function, based upon the training input data received and the training output data received, to determine a trained function; and an output interface to output the trained function.

At least one embodiment of the inventive application is directed to a medical imaging facility, comprising:

the positioning quality determination facility of an embodiment; and a training facility, comprising:

a first training interface to receive input training data including image data of test persons of a training database;

a second training interface to receive output training data, assigned to the input training data, the output training data including landmarks assigned to at least one first subsection of an apparatus insertable into a body of a patient and an at least one second subsection of the apparatus insertable into the body of the patient, and including data for identifying and localizing the at least one first subsection of the apparatus insertable into the body of the patient and second subsection of the apparatus insertable into the body of the patient;

a training unit to train a function, based upon the training input data received and the training output data received, to determine a trained function; and an output interface to output the trained function.

At least one embodiment of the inventive application is directed to a non-transitory computer program product storing a computer program, directly storable in a storage facility of a data processing facility, including program sections to carry out the method of an embodiment when the computer program is carried out in the data processing facility.

At least one embodiment of the inventive application is directed to a non-transitory computer-readable medium storing program sections, readable in and executable by a computer unit, to carry out the method of an embodiment when the program sections are executed by the computer unit.

BRIEF DESCRIPTION OF THE DRAWINGS

The invention is described and explained in more detail below based upon the example embodiments shown in the figures.

The drawings show.

DETAILED DESCRIPTION OF THE EXAMPLE EMBODIMENTS

Figure 1:
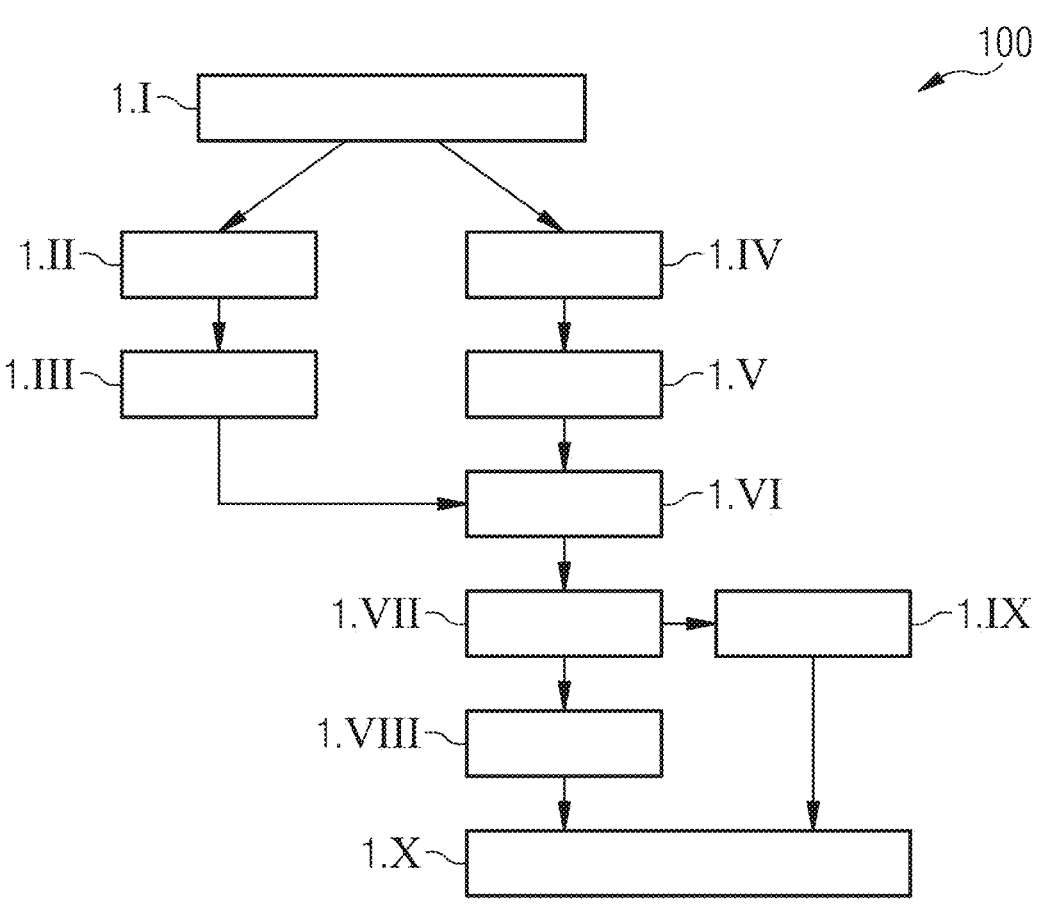
FIG. 1 a flow chart for illustrating a conventional method for the automated detection of an external apparatus inserted into a patient's body, FIG. 2 a schematic representation of typical insertion paths of a central venous catheter in a human body and the statistical distribution of the position of the catheter tips, FIG. 3 a flow chart, which illustrates a method for determining a positioning quality of an external apparatus inserted into a patient's body according to an example embodiment of the invention, FIG. 4 a flow chart which illustrates a method for providing a trained function according to an example embodiment of the invention, FIG. 5 a schematic representation of input vectors and output vectors for the training method shown in FIG. 4, FIG. 6 a schematic representation of a positioning quality determination facility according to an example embodiment of the invention, FIG. 7 a schematic representation of a training facility according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CDROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

With at least one embodiment of the inventive method for determining a positioning quality of an external apparatus inserted into a patient's body, image data is detected from the patient's body. This image data comprises information relating to the inside of a patient. In particular, the external apparatus in the inside of the body of the patient is also mapped onto the image data. An apparatus inserted into the body of a patient by way of a body opening or a vessel or an artificially created opening is to be understood to mean an external apparatus. Furthermore, one or more first anatomical landmarks are detected in or with a first subregion, in which the apparatus is positioned as expected.

The method of at least one embodiment is not restricted to the detection of an anatomical first landmark or a first subregion. A number of first landmarks can also be used in order to determine a subregion or, based upon several landmarks, several subregions, which represent a number of points of entry for the external apparatus or a number of apparatuses, for instance, can also be determined. The external apparatus is also then positioned in this first subregion if it continues possibly to be incorrectly positioned in the body of the patient.

One such "safe" subregion can lie, for instance, in an entry area of the external apparatus, past which, for anatomical reasons, the external apparatus must also move in the case of a further misalignment. A first subsection of the external apparatus is then sought in or with the first "safe" subregion. The already mentioned first anatomical landmark, with which the first subregion or the first subsection can be determined, is located in this first subregion or close to this subregion, i.e. in a subregion adjacent to the first subregion. In the case that the first subsection of the external apparatus has been successfully detected, at least one second anatomical landmark is detected in or with at least one second subregion, through which the external apparatus runs as expected and which comprises a clinically relevant region. One such second subregion comprises, for instance, the desired subregion for the second subsection of the apparatus.

A clinically relevant region is to be understood to mean a region which is vital for the intended effect of the apparatus or with which or in the radius of which an incorrect positioning of the second subsection could possibly have adverse effects on the health of the patient.

The second subsection of the external apparatus is then detected in or with the second subregion based upon the already localized first subsection of the external apparatus. Here, based upon the first subsection, a continuation of the external apparatus is sought in the image data and traced as far as the second subsection. When the continuation of the external apparatus is traced, the course of the external apparatus with respect to the occurrence of loops or bends can also be checked at the same time. Defects in the external apparatus can be identified and possibly eliminated in this way. Finally, a quality of the positioning of the at least one second subsection of the external apparatus is determined by measuring a gap between the localized second subsection of the external apparatus and the at least one second landmark. For instance, the right atrium and the carina are used together as landmarks for the localization of a central vein catheter.

The search steps and identification steps mentioned can also be carried out repeatedly one after the other or simultaneously if accordingly several apparatuses or several sections of apparatuses are to be monitored. The search steps mentioned can preferably be carried out automatically, i.e. the image data analysis is preferably carried out automatically so that human errors can be ruled out. Moreover, the evaluation can take place over a short time, preferably even in real time, by way of the automated image data analysis.

Therefore during a longer period of time, in which the apparatus is located in the patient, updated quality data can be provided and in this way the safety of the patient can be increased and qualified staff can be spared or the qualified staff can limit their attention to more challenging tasks, such as, for instance, individual steps of an operation or another treatment of the patient.

Furthermore, the detection of the apparatus by the use of anatomical landmarks can be limited to apparatus-specific subregions in the image data, in or with which the apparatus is to be found, if it is located in the body of the patient at all. One such reduction in an image section to be sought accelerates the image analysis or reduces the requirements on the computing capacity required to evaluate the image data.

By following the course of the external apparatus up to a clinically relevant subsection or a corresponding subregion in the body, based on a detected subsection, the object of determining the position of the external apparatus in the body is significantly simplified and the certainty that the external apparatus was also actually identified correctly is increased. By the second anatomical landmark being used for quality assessment purposes, which is located at a defined anatomical position, the relative position of which is known at a desired position of the second subsection of the external apparatus, via one or more simple measurements, for instance of the gap or the angle, an objective quality criterion can be produced for the determined position of the second subsection of the external apparatus.

The quality criterion is dependent here upon a previously known physical measure, for instance a gap or angle, between the second anatomical landmark and the desired position of the second subsection of the external apparatus and the actual dimension measured based upon the image data, preferably a gap or angle, between the second subsection of the external apparatus and the second landmark. The use of anatomical landmarks to check the positioning quality can be reproduced and configured advantageously. Here the visualization of anatomical landmarks and their gaps or angles relating to lines or conductors provides a radiologist with access which is easy to understand and is more easily understood than a scalar probability value, which has been estimated by what is known as a black-box approach. Furthermore, the measurement of a position quality based upon anatomical landmarks allows for a subjective adjustment to individual preferences of a user.

With at least one embodiment of the inventive method for providing a trained function, input training data is received, which comprises medical image data of test persons of a training database. This method is suited in particular to the case in that the identification and localization of the landmarks and/or the subsections of the apparatus is to take place by applying artificial intelligence or in an AI-based manner. In order to realize such an approach, a function is trained by applying a machine learning, for instance realized by an artificial neural network. To this end, output training data, which is assigned to the input training data, is received in addition to the input training data. Here the output training data comprises landmarks which are assigned to a first and a second section of an external apparatus inserted into a patient's body, as well as data for identifying and localizing the first and second section of the apparatus inserted into a patient's body. Furthermore, a function is trained via an algorithm based on machine learning based upon the input data and the output data. Advantageously, no complex model approach for determining the function needs to be laboriously designed, but the function is instead produced automatically based upon the available database of training data. In particular, with a large number of different parameters to be taken into account or a phenomenon which cannot be detected adequately by a model, one such procedure will outclass the purely model-based approach.

At least one embodiment of the inventive positioning quality determination facility has an input interface for detecting image data from a patient's body. At least one embodiment of the inventive positioning quality determination facility also comprises a landmark detection unit for AI-based detection of first anatomical landmarks in or with at least one first subregion, in which an external apparatus is positioned as expected. At least one embodiment of the inventive positioning quality determination facility also comprises an identification unit for preferably AI-based searching and localizing of at least one subsection of the external apparatus in or with the at least one first subregion. Here the landmark detection unit is designed, in the case that the external apparatus has been detected in or with the first subregion, to identify and localize at least one second landmark in or with at least one second subregion, through which at least one second section of the external apparatus runs as expected and which comprises a clinically relevant region. The identification unit is furthermore designed to localize the external apparatus in or with the at least one second subregion based upon the already localized subsection of the external apparatus. The positioning quality determination facility comprises a quality determination unit for determining a quality of the positioning of the second subsection of the external apparatus by measuring a physical dimension, for instance a gap or angle between the localized external apparatus and the at least one second landmark.

At least one embodiment of the inventive training facility has a first training interface for receiving input training data, which comprises medical image data of test persons of a training database. At least one embodiment of the inventive training facility also comprises a second training interface for receiving output training data, which is assigned to the input training data. Here the output training data comprises landmarks, which mark a previously known position of a first subsection and a desired position or a position, to be checked, of a second subsection of an apparatus inserted into a patient's body, as well as data for identifying and localizing the first and second subsection of the apparatus inserted into a patient's body. Part of at least one embodiment of the inventive training facility is also a training unit for training a function based upon the training input data and the training output data and an output interface for outputting the trained function. The inventive training facility shares the advantages of the inventive training method.

At least one embodiment of the inventive imaging medical facility has the positioning quality determination facility and the inventive training facility. At least one embodiment of the inventive imaging medical facility combines the advantages of at least one embodiment of the inventive positioning quality determination facility and at least one embodiment of the inventive training facility.

The essential components of at least one embodiment of the inventive positioning quality determination facility and the inventive training facility can be embodied predominantly in the form of software components. This relates in particular to the landmark detection unit and the identification unit of the positioning quality determination facility and the training unit of the training facility.

Essentially these components can however also be realized to some extent, particularly if it involves particularly rapid calculations, in the form of software-assisted hardware, for instance FPGAs or suchlike. Similarly the required interfaces, for instance when it only involves a takeover of data from other software components, can be embodied as software interfaces. They can also be configured as interfaces constructed from hardware, which are controlled by suitable software.

A realization largely through software has the advantage that even medical imaging facilities which have previously been used can be easily set up by a software update to operate in the inventive manner, possibly by retrofitting the requisite hardware. In this respect, the object is also achieved by a corresponding computer program product with a computer program which can be loaded directly into a storage facility of a medical imaging facility and comprises program portions in order to carry out all the steps of the inventive method when the computer program is executed in the medical imaging facility.

Such a computer program product can comprise, where relevant, in addition to the computer program, further constituents, such as, for example, documentation and/or additional components including hardware components, for example, hardware keys (dongles, etc.) in order to use the software.

By way of a software implementation, the methods can be carried out in a reproducible and less error-prone manner on different medical imaging facilities.

For transport to the storage facility of the medical imaging facility and/or for storage at the medical imaging facility, a computer-readable medium, for example, a memory stick, a hard disk or another transportable or permanently installed data carrier can be used, on which the program portions of the computer program which can be read in and executed by a data processing facility, for instance a computer unit, are stored. For this purpose, the computer unit can have, for example, one or more cooperating microprocessors or the like.

The claims and the description below each contain particularly advantageous embodiments and developments of the invention. Here the claims of one claim category can in particular also be developed analogously to the dependent claims of another claim category. In addition, in the context of the invention, the different features of different example embodiments and claims can also be combined to form new example embodiments.

Preferably, with at least one embodiment of the inventive method for determining a positioning quality of an external apparatus inserted into a patient's body, at least one of the localization steps or detection steps takes place based upon artificial intelligence. For instance, the detection of the at least one first landmark takes place by applying artificial intelligence, abbreviated to AI. The at least one first landmark typically comprises one or more particularly prominent body parts which are easy to find, which is/are located as expected in the vicinity of a first section of the external apparatus to be found. However, one such body part, for instance the collar bone of a patient, can deviate clearly from an ideal form, so that a model-based approach would possibly have a lower hit rate. Even the external apparatus inserted into the body of a patient can preferably be more easily identified with an AI-based approach, since even when individual subsections of the external apparatus are found, individual anatomical factors or differences from apparatuses of the same type can be taken into account more flexibly and effectively by the AI-based approaches.

With at least one embodiment of the inventive method for determining a positioning quality of an external apparatus inserted into a patient's body, the at least one first subregion comprises at least one point of entry of the external apparatus into the patient's body. If a point of entry is known, which is inevitably the case since the insertion of the external apparatus must be carried out in advance through the point of entry, the position of the at least one first subregion, in which the point of entry is located, is also easy to localize. The discovery is still facilitated in that at least one first landmark is localized, which is positioned in or close to this at least one first subregion.

With at least one embodiment of the inventive method for determining a positioning quality of an external apparatus inserted into a patient's body, the at least one second anatomical landmark is localized in a subregion in or with which, in other words possibly in the neighboring region thereof, the position of an end section of the external apparatus is to be expected. One such end section of an external apparatus to be inserted into the body of a patient is a crucial functional element, for instance a catheter tip or a probe head, with which a possibly vital body function of a patient is to be maintained or supported. For the localization of this end section, it is therefore particularly important for its positioning to be correct, so that it can also realize its vital function.

The external apparatus inserted into a patient's body can comprise the following apparatus types, for instance:
    a central venous catheter, which is inserted by way of a vein of a patient,
    a peripherally inserted central catheter, which is inserted by way of a vein of an arm of a patient,
    an endotracheal probe, which is inserted by way of the mouth and the trachea of a patient,
    a nasogastric probe, which is inserted by way of the nose of a patient.

If the tip of a venous catheter is now incorrectly inserted or positioned, for instance, this may result in a blockage in the blood flow or in a thrombosis. With an incorrectly inserted probe, be it through the mouth or the nose, a patient may begin to choke, for instance, if, as a result, the respiratory system of the patient concerned becomes blocked. It is therefore crucial that the end section of the external apparatus, which is preferably the second subsection of the external apparatus, for instance a catheter tip or a probe tip, is located at the correct position. Advantageously, complications even to the extent of the patient dying are avoided by the preferably automated monitoring of this position.

Preferably, with the inventive method for determining a positioning quality of an external apparatus inserted into a patient's body, one of the following landmark types is used as a first anatomical landmark:
    the trachea,
    the spinal column,
    a long bone.

A region, in which a number of important vessels converge, is preferably selected as a first subregion. It can advantageously be considered to be guaranteed that the external apparatus inserted into the body of a patient is correctly positioned as far as the branching. It is then of interest at the branching to question whether the external apparatus continues to run correctly at the branching. Since a first section of the external apparatus has been found in the first subregion, a course of the external apparatus through the correct branching can now be checked by tracing the external apparatus from this position.

The trachea is suited for instance as a marker or landmark for the introduction of probes inserted into the respiratory tract. The spinal column runs in the longitudinal direction of the body and is suited as a landmark particularly for apparatuses which run longitudinally in the body. A long bone can likewise effectively reproduce or mark the course of an apparatus which runs in the longitudinal direction of the body, in particular the direction of this course.

The collar bone, which is positioned close to a point of entry of an apparatus in the top trunk area or neck area, is also well suited to marking a point of entry of an external apparatus.

With at least one embodiment of the inventive method for determining a positioning quality of an external apparatus inserted into a patient's body, the localization of the external apparatus is carried out in or with the at least one second subregion preferably based upon the already localized first subsection of the external apparatus by continuously pursuing the localization of the apparatus beyond the subregion of the at least one first subsection. During the search for the apparatus in the at least one second subregion, the at least one first subregion, in which the external apparatus is definitely located, is advantageously used as a starting point.

Now the course of the external apparatus can be detected based upon image data and possibly traced as far as the second subregion or the second subsection of the external apparatus, so that the sought second subsection, which is best located in the second subregion, is easy to find.

A localization of the external apparatus or of subsections of the external apparatus is carried out particularly preferably by a targeted search for a specific type of such an apparatus. If, for instance, the shape of the at least one first subsection and/or the at least one second subsection of the external apparatus is known, the respective subsection in a medical image representation can be discovered more easily. An expected course of an external apparatus in the body of the patient also depends in most instances on its type. If the expected course of the external apparatus is known, this can be used for locating a subsection, in particular the end section of the external apparatus. Advantageously, different apparatuses which are also present at the same time can be separated into medical image data in accordance with different types. This possibility is then particularly important if individual external apparatuses cross on the image or at least touch so that a further course of an external apparatus is not readily identifiable.

A classification of the external apparatus particularly preferably takes place in the localization according to at least one of the following criteria:

a different thickness, a different appearance, a different color.

Advantageously different apparatuses which are inserted into the body of a patient or run on the surface of the body can now be distinguished more easily from one another even when they are in contact with one another on the image data. For instance, a catheter can be distinguished from an EKG cable on account of its thickness. The appearance of individual sections of a catheter or a probe also differ from the EKG cables. Even the color of the different apparatuses or their patterning can be used at least indirectly for distinction purposes.

If a tube is brighter, for instance, this means less x-ray transparency. This is a feature which allows different tubes to be differentiated (e.g. tubes with or without guided liquids). Otherwise, there are tubes whose walls are produced from specific materials and thus have a continuous or regularly changing tissue-pattern color course.

FIG. 1 shows a flow chart 100 for illustrating a conventional method for the automated detection of an external apparatus inserted into a patient's body, in this case a catheter. In step 1.I, AI is used to determine whether the catheter is present in an image representation. Since it is not known where the catheter is located, the entire image is typically subjected to an AI-based evaluation. If it is determined in step 1.I that the catheter is present, a catheter segmentation is performed in step 1.II. With the optional step 1.III, an instance separation is then carried out.

The step of instance separation comprises an optional step of preparing the segmentation results. If a number of regions in the image which are separated from one another are segmented, it is possible to determine based upon criteria whether all segmented regions correspond to the desired object or are to be assigned to this or have been incorrectly produced, on account of artifacts, for instance.

In step 1.IV, an ROI (region of interest=target area) is detected, in which the catheter is located. For this step, an active contour model or a neural network can be used. In the step 1.V, what is known as a seed or a starting point is selected for an automatic or manual tracing of a catheter.

Subsequently, in step 1.IV, what is known as catheter tracing, in other words a tracing of the catheter, is carried out. The separated instances are also to be added to the catheter tracing. Furthermore, in the step 1.VII, a catheter classification is carried out. For instance, there are types of catheters with a tip or with two tips, which are separated during this classification. With the step 1.VIII, a localization of the tip(s) of the catheter is performed. A vein catheter has, for instance, a tip at the lower end, which is identified and localized in this step. In addition, in the step 1.IX, a classification of a position of the catheter is carried out as normal or abnormal. Finally, in the step 1.X, an end result of the quality check is communicated.

Figure 2:
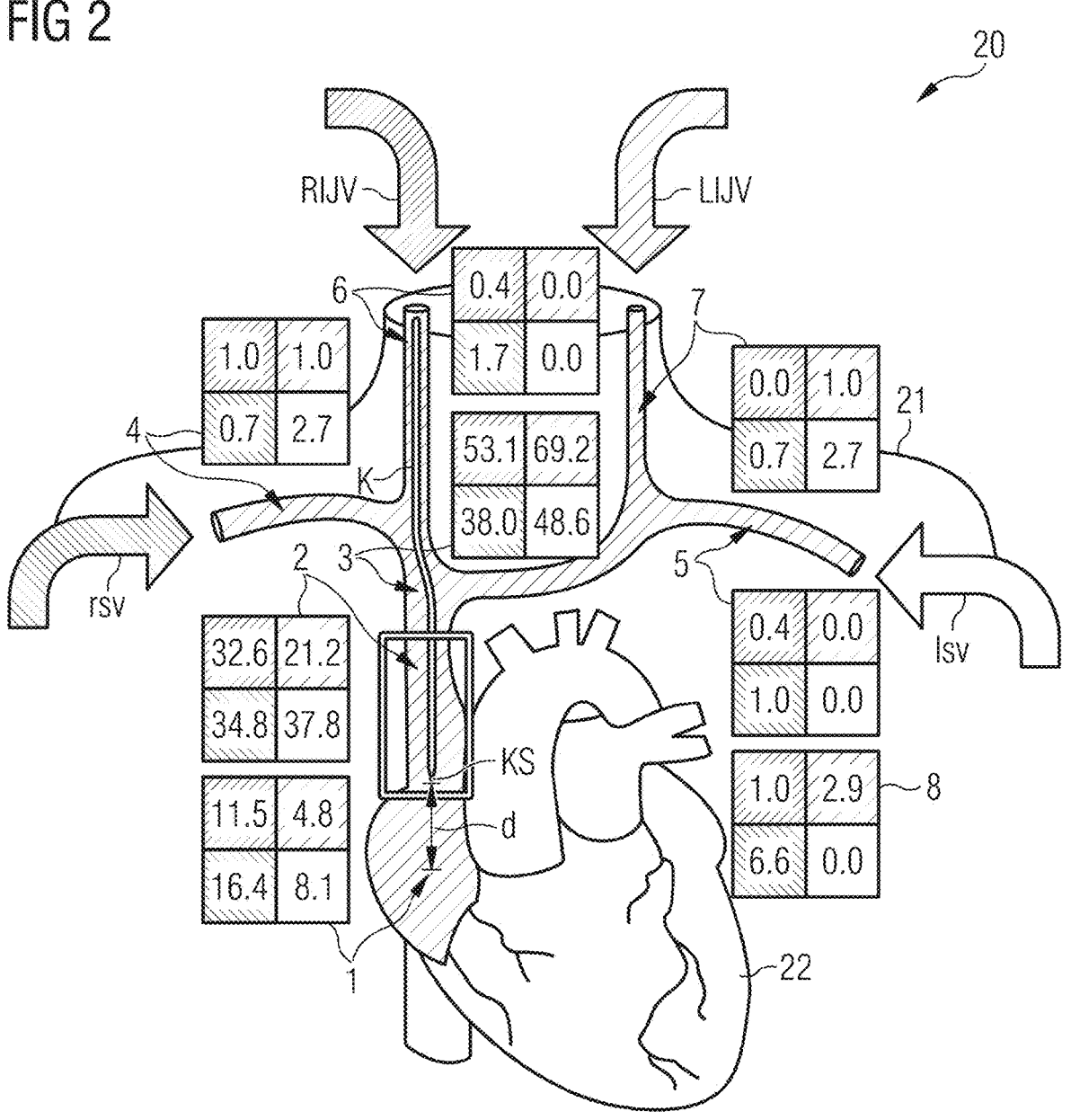

FIG. 2 shows a schematic representation 20 of typical insertion paths of a central venous catheter K in a human body 21 and the statistical distribution of the position of the catheter tip KS by way of the digits 1, 2, 3, 4, 5, 6, 7 and 8. The left and right subclavian vein rsv, lsv in the region of the right and left collarbone, to which the digits 4 and 5 are assigned, and the right and left internal jugular veins RIJV, LIJV in the left and right neck area, to which the digits 6 and 7 are assigned, are shown as insertion inlets. By way of example, FIG. 2 shows that the catheter K has been inserted by way of the right internal jugular vein RIJV, and the catheter tip KS is positioned in the vena cava, which is marked in FIG. 2 with a rectangular box and the digit 2.

The percentages, specified in four squares in each case, which are assigned to the respective digits 1 to 8, specify the probabilities of the occurrence of the catheter tip KS, when it has been inserted through one of the four cited points of entry RIJV, LIJV, rsv, lsv. Here the square, top left, is assigned to the right internal jugular vein RIJV as a point of entry, the square, top right, is assigned to the left internal jugular vein LIJV as a point of entry, the square, bottom left, is assigned to the right subclavian vein rsv as a point of entry and the square, bottom right, is assigned to the left subclavian vein lsv as a point of entry. For instance, the left upper square, in addition to the digit 2, specifies a probability of 32.6 percent that the catheter tip KS is positioned in the region 2 of the upper vena cava when inserted by way of the right internal jugular vein RIJV. The monitoring of the insertion of a central venous catheter K can now take place by determining anatomical landmarks as reference points. For instance, the collar bone in the regions 4, 5 and the transverse process as far as the sternoclavicular articulation can be used as landmarks in order to mark the entry regions of a central vein catheter K. By detecting the landmarks, a small image section can be extracted, in which a section of a central vein catheter K can be identified or classified based upon AI. FIG. 2 also identifies that the upper vena cava, which is marked with the digit 2, is the preferred position for the catheter tip KS. In order to clarify this situation, this region is marked by a rectangular frame. There is therefore a possibility of being able to determine the quality of the positioning of the catheter tip KS, of detecting the right atrium of the heart 22, which is marked in FIG. 2 with the digit 1, as a second landmark, of restricting a subregion which is close thereto, in order to localize and identify the catheter tip KS in the subregion based upon AI and to determine a positioning quality by measuring a gap d between the localized catheter tip KS and the second landmark, i.e. the center of the right atrium. Applications exist in which the position 2 of the vena cava is the optimal position. With some applications, it is however also sufficient if the catheter tip KS is located in the region 3. With the inventive method, according to one application it is possible to inspect another region for the catheter tip KS.

Figure 3:
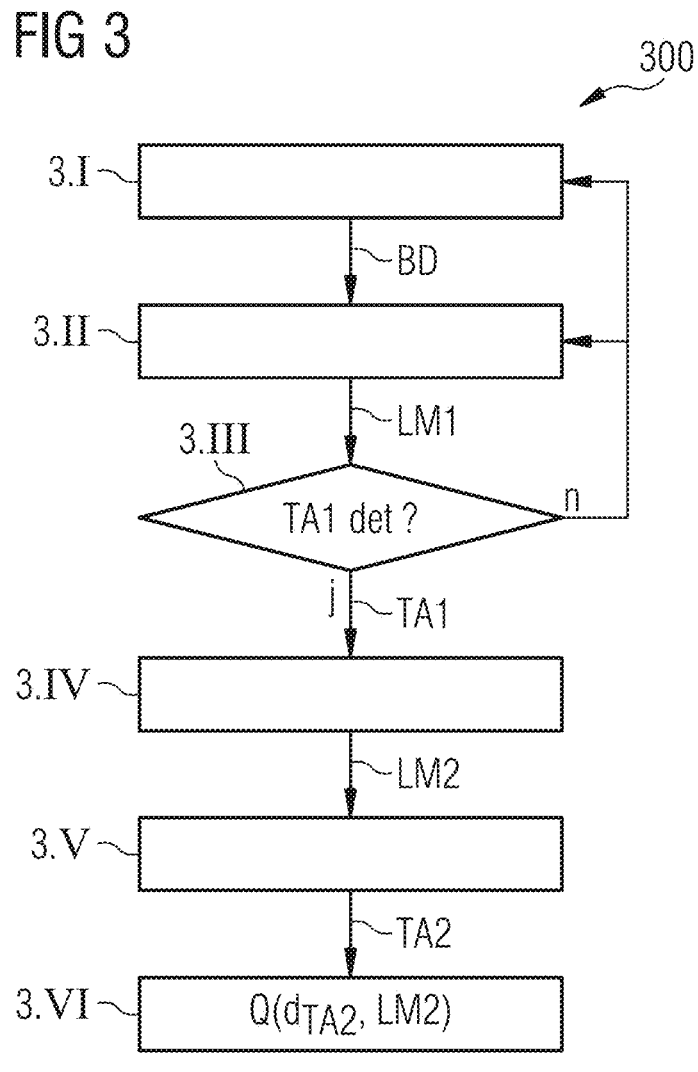

FIG. 3 shows a flow chart 300, which illustrates a method for determining a positioning quality of a catheter inserted into a patient's body according to an example embodiment of the invention. In the step 3.I, image data BD of the patient's body is detected. For instance, x-ray image data of the relevant patient is detected or received and maps the catheter in the body of the patient. Then, in the step 3.II, first anatomical landmarks LM1 of a first subregion, in which the catheter is positioned as expected, are detected. The detection is carried out automatically by applying an artificial neural network, wherein the image data only of the first subregion is evaluated with respect to landmarks suspected there. The first subregion comprises for instance the left, internal jugular vein LIJV marked in FIG. 2 with the digit 7. Since the catheter has been inserted into the body of the patient by way of the left internal jugular vein LIJV, it is known to the monitoring person that the catheter has to pass in the first subregion. Typical landmarks in this region are the collar bone and the transverse process as far as the sternoclavicular articulation.

In step 3.III, a subsection TA1 of the catheter is now sought in the first subregion. For instance, the search is carried out on an AI basis by evaluating the image region of the first subregion. In the case that a catheter section TA1 is detected in the first subregion, which is identified in FIG. 3 with "y", a move is made to step 3.IV, in which a second landmark LM2 is determined or localized in a second subregion, in which the tip TA2 of the catheter is located as expected. One such subregion comprises for instance the upper vena cava or upper hollow vein, through which the blood which is low in oxygen is pumped to the right atrium of the heart. The right atrium of the heart, which is also referred to as right atrium and is particularly easy to localize, is also suitable, for instance, as a second landmark LM2. In the step 3.V, an AI-based detection of the catheter tip is then carried out in subregions adjoining the right atrium of the heart, such as, for instance, the upper vena cava. If the catheter tip in one of the subregions is found in the vicinity of the right atrium, in the step 3.VI, a quality Q of the positioning of the catheter tip in the clinically relevant region is determined by measuring a gap dTA2 between the localized catheter tip TA2 and the second landmark LM2.

Figure 4:
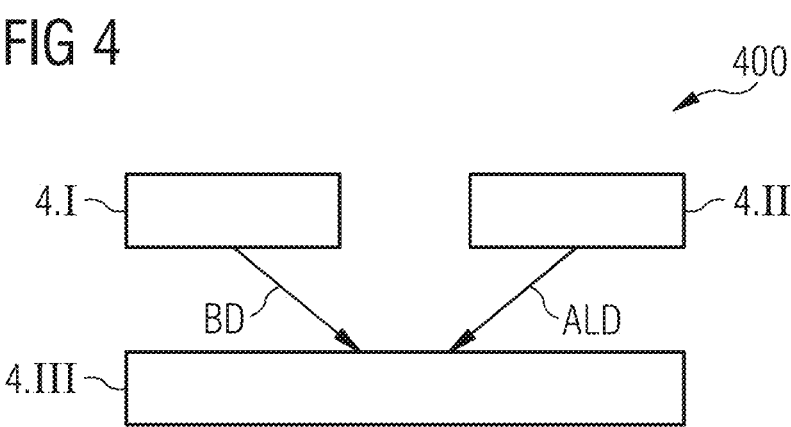

FIG. 4 shows a flow chart 400, which illustrates a training method, in other words a method for providing a trained function F for localizing a landmark LM1, LM2 or for detection of a first section TA1 or a second section TA2 of a catheter.

In step 4.I, input training data, in this case image data BD, is firstly received from a database, for instance, which comprises individual case data of images of catheterized persons from a training database, in which the course of the catheter in the body is already known. Furthermore, in the step 3.II, already known labeled output data ALD assigned to the input training data BD is received, which comprises the sought first and second landmarks LM1, LM2 and subsections TA1 or TA2 of the catheter or its positions PTA1, PTA2 and are to be assigned to the respective image data BD of the respective catheterized person.

Finally, in the step 4.III, a training of an artificial neural network is carried out based upon the input training data BD and the output training data ALD. It should be mentioned here that the method shown in FIG. 3 has multiple stages. Since overall it contains four search steps, in which an AI-based function can be used. Objects to be sought are considered here to be the first landmark LM1, the first catheter subsection TA1 or its position PTA1, the second landmark LM2, the second catheter subsection TA2 or its position TA1. The input data for the next step comprises, aside from the image data BD, also the output data of the preceding steps or the data found in the preceding steps, i.e. in particular the first landmark LM1 and the first subsection TA1 or its position PTA1 and the second landmark LM2. Since the respective output data is known, the different functions F1, F2, F3, F4 can be trained separately for the individual search steps.

Figure 5:
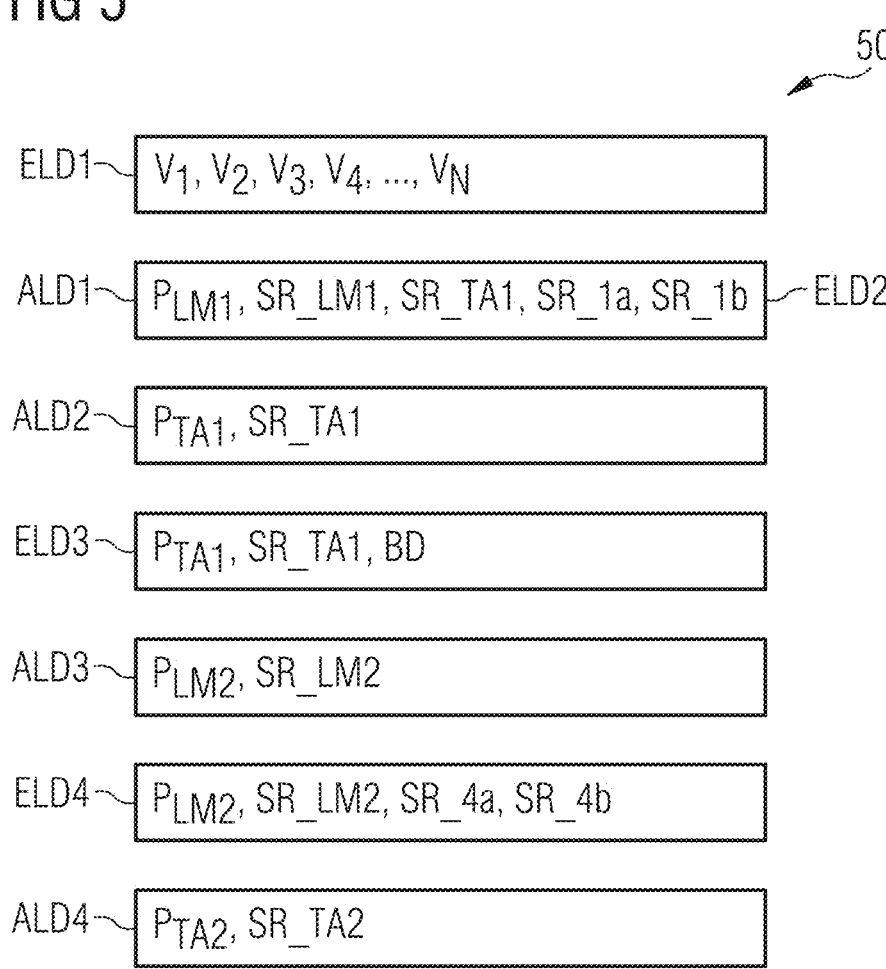

FIG. 5 shows a schematic representation of an individual training data record 50 of an individual test person from a database with an input training data vector BD and an output training data vector ALD.

A first input training data vector ELD1 comprises, for instance, the overall image data BD, in which a first landmark LM1, for instance a sternoclavicular articulation, is sought, with a plurality of voxels V1, V2, V3, . . . , VN. The output training data vector ALD1 then comprises the position PLM1 of the first landmark LM1, the associated subregion SR_LM1 and adjoining subregions SR_TA1, SR_1a, SR_1b etc., which are required for the training of the first search function F1 for the first search step. The body of a patient is divided for instance into a plurality of k subregions SR_1a, SR_1b etc, to which are assigned in each case a sub quantity BD1, BD2, BD3, . . . , BDk of the voxels V1, V2, V3, . . . , VN of the overall image data BD, which comprise N image points for the image representation of an inside of the body of a test person.

A second input training data vector ELD2, which is required for the second search step, now comprises the output training data ALD1 as input training data ELD2, in other words the subregion SR_LM1 of the sternoclavicular articulation as well as adjoining subregions SR_TA1, SR_1a, SR_1b or the image data BD1, BD1a, BD1b assigned to these. Here $1 < 1a$, $1b <= k$. The second function F2 to be trained now searches for a first catheter section TA1 in the cited candidate regions SR_LM1, SR_TA1, SR_1a, SR_1b. The position of the first catheter section PTA1 and the associated subregion SR_TA1 are therefore used as a second output training data ALD2.

A third input training data vector ELD2 now comprises the position of the first catheter section PTA1, the associated subregion SR_TA1 and the overall image data BD. A third function F3 to be trained is now used to continue the catheter from the subregion SR_TA1 of the catheter section PTA1. To this end, subregions SR_3a, SR_3b, SR_LM2 of the image data BD which adjoin the subregion SR_TA1 and subregions adjoining this in each case are searched through by the function to be trained until a second landmark LM2 has been found. The position of the second landmark PLM2 and the subregion SR_LM2 of this second landmark LM2, for instance the right atrium of the heart, is then used as a third output training data vector ALD3.

As a fourth input training data vector ELD4, the subregion SR_LM2 and the adjoining subregions SR_4a, SR_4b and the second landmark LM2 or its position PLM2 are used.

The fourth output training data ALD4 comprises the sought subregion SR_TA2 of the sought catheter tip and its position PTA2.

Based upon a plurality of such training data records 50, artificial neural networks F1,F2,F3,F4 can now be trained so that they carry out the cited intermediate steps for any image representation to be examined and determine the subregion in the image BD in which the catheter tip is located.

Figure 6:
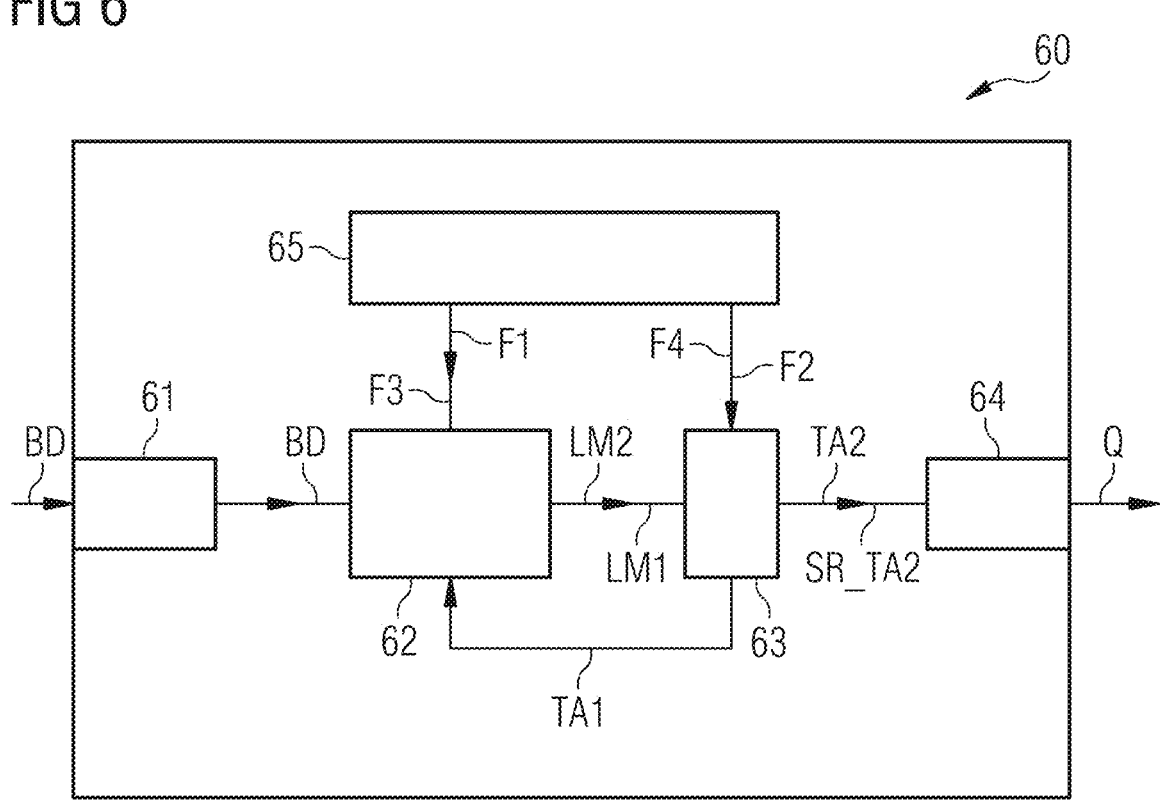

FIG. 6 shows a schematic representation of a positioning quality determination facility 60 according to an example embodiment of the invention. The positioning quality determination facility 60 comprises an input interface 61 for detecting image data of a patient body of a patient. Part of the positioning quality determination facility 60 is also a landmark detection unit 62 for the AI-based detection of first anatomical landmarks LM1 of a first subregion SR_LM1, in which a catheter section is positioned as expected. For the AI-based detection of the landmarks LM1, a first function F1 which has been trained for this detection, is obtained from a database 65. The determined first subregion SR_LM1 and the image data BD are transmitted to an identification unit 63 for the AI-based localization of a subsection TA1 of the catheter in or with the first subregion SR_LM1, which is likewise part of the positioning quality determination facility 60. For the AI-based detection or localization of the first subsection TA1, a second function F2 is obtained from a database 65, which has been trained for this detection. The determined subsection TA1 and its subregion SR_TA1 are transmitted to the landmark detection unit 62, which is designed to determine a second landmark LM2 in a second subregion SR_LM2, in the vicinity of which the catheter tip is located. For the AI-based detection of the second landmark LM2, a third function F3 which has been trained for this detection is obtained from a database 65. The determined second landmark LM2 and its subregion SR_LM2 are transmitted to the identification unit 63, which is designed to find or localize the catheter tip by continuing the catheter from the first subregion SR_TA1. For the AI-based detection of the catheter tip, a fourth function F4 is obtained from a database 65, which has been trained for this detection. The information in relation to the determined catheter tip TA2 and its subregion SR_TA2 are transmitted to a quality determination unit 64. The quality determination unit 64 is designed to determine a quality Q of the positioning of the catheter tip in the clinically relevant region by measuring a distance d of the localized catheter tip TA2 from the second landmark LM2.

Figure 7:
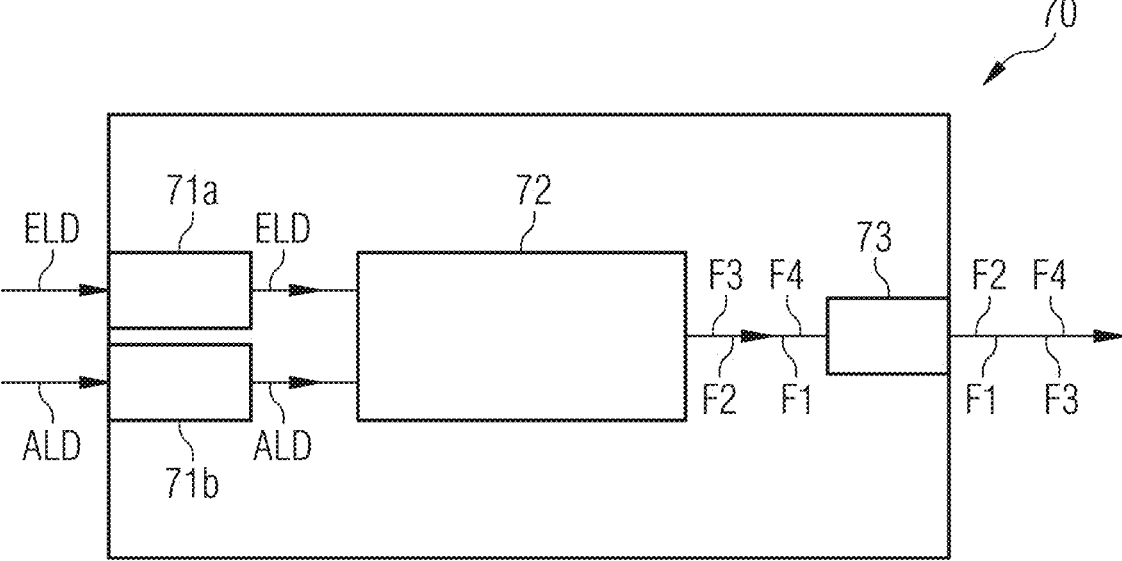

In FIG. 7, a training facility 70 according to an example embodiment of the invention is shown schematically. The training facility 70 comprises a first training interface 71$a$ for receiving input training data ELD, which comprises the design illustrated in FIG. 5, as well as a second training interface 71$b$ for receiving output training data ALD, actually output training data ALD1, ALD2, ALD3, ALD4, which is assigned to the input training data ELD, actual input training data ELD1, ELD2, ELD3, ELD4, wherein the input training data ELD and the output training data ALD have the design shown in FIG. 5 in each case. The training facility 70 moreover comprises a training unit 72, which is designed to train an artificial neural network based upon the training input data ELD and the training output data ALD. Furthermore, the training facility 70 also comprises an output interface 73 for outputting the generated artificial neural network F1, F2, F3, F4 to a database 65 (see FIG. 6).

Finally, it should again be noted that the methods and devices described above are merely preferred example embodiments of the invention and that the invention can be modified by a person skilled in the art without departing from the field of the invention, insofar as it is specified by the claims. For the sake of completeness, it should be noted that the use of the indefinite articles "a" or "an" does not preclude the relevant features from also being present plurally. Similarly, the expression "unit" does not preclude this consisting of a plurality of components which can possibly also be spatially distributed.

Although the invention has been illustrated and described in detail by the preferred embodiments, the invention is not limited by the disclosed examples and other variations can be derived herefrom by the person skilled in the art without departing from the scope of protection of the invention.

Even if not explicitly stated, individual example embodiments, or individual sub-aspects or features of these example embodiments, can be combined with, or substituted for, one other, if this is practical and within the meaning of the invention, without departing from the present invention. Without being stated explicitly, advantages of the invention that are described with reference to one example embodiment also apply to other example embodiments, where transferable.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a positioning quality of an apparatus inserted into a body of a patient, the method comprising:

detecting image data of the body of the patient, the image data representing the apparatus inside the body of the patient;

detecting at least one first anatomical landmark in or adjacent to at least one first subregion, the at least one first subregion including a point of entry of the apparatus into the body of the patient;

searching for at least one first subsection of the apparatus in or adjacent to the at least one first subregion;

detecting at least one second anatomical landmark in or adjacent to at least one second subregion, the apparatus being expected to proceed into the at least one second subregion, and the at least one second subregion including a clinically relevant region;

detecting and localizing at least one second subsection of the apparatus in or adjacent to the at least one second subregion based on the at least one first subsection of the apparatus to determine a localized at least one second subsection of the apparatus; and determining a quality of positioning of the at least one second subsection of the apparatus by measuring a dimension between the localized at least one second subsection of the apparatus and the at least one second anatomical landmark.

2. The method of claim 1, wherein at least one a portion of the method is carried out based on AI.

3. The method of claim 1, wherein the at least one second anatomical landmark is in a third subregion in or adjacent to which a position of an end section of the apparatus is expected.

4. The method of claim 1, wherein the apparatus comprises one of:

a central venous catheter insertable into the body of the patient by way of a first vein;

a peripherally inserted central catheter insertable into the body of the patient by way of a vein of an arm of the patient;

an endotracheal probe insertable into the body of the patient by way of a mouth of the patient and a trachea of the patient; or a nasogastric probe insertable into the body of the patient by way of a nose of the patient.

5. The method of claim 1, wherein the at least one first anatomical landmark is at least one of one of:

a trachea of the patient;

a spinal column of the patient; or a long bone of the patient.

6. The method of claim 1, wherein the localizing the at least one second subsection of the apparatus localizes the at least one second subsection of the apparatus based on the at least one first subregion of the apparatus by continuously localizing the at least one first subsection of the apparatus beyond at least one third subregion, the at least one third subregion including the at least one first subsection, and the at least one third subregion being included in or adjacent to the at least one first subregion.

7. The method of claim 1, wherein the at least one first subregion is selected as a region in which a number of vessels converge.

8. The method of claim 1, wherein the searching for the at least one first subsection of the apparatus searches for the at least one first subsection of the apparatus based on a first targeted search for a specific type of the apparatus; or the localizing the at least one second subsection of the apparatus localizes the at least one second subsection of the apparatus based on a second targeted search for the specific type of the apparatus.

9. The method of claim 1, further comprising:

classifying the apparatus based on at least one of:

a thickness, an appearance, or a color.

10. A positioning quality determination device, comprising:

an input interface configured to detect image data from a body of a patient, the image data representing an apparatus inside of the body of the patient; and first processing circuitry configured to cause the positioning quality determination device to, detect at least one first anatomical landmark in or adjacent to at least one first subregion, the at least one first subregion including a point of entry of the apparatus into the body of the patient, search for and localize at least one first subsection of the apparatus in or adjacent to the at least one first subregion, detect at least one second landmark in or adjacent to at least one second subregion based on the at least one first subsection of the apparatus being detected in or adjacent to the at least one first subregion, the apparatus being expected to proceed into the at least one second subregion, and the at least one second subregion including a clinically relevant region, localize at least one second subsection of the apparatus in or adjacent to the at least one second subregion based on the at least one first subsection of the apparatus to determine a localized at least one second subsection of the apparatus; and determine a quality of positioning of the at least one second subsection of the apparatus by measuring a dimension between the localized at least one second subsection of the apparatus and the at least one second landmark.

11. A medical imaging device, comprising:

the positioning quality determination device of claim 10; and a training device including, a first training interface to receive input training data including image data of a training database, and image data being of test persons, a second training interface to receive output training data assigned to the input training data, the output training data including landmarks and first data, the landmarks being assigned to at least one first subsection of an apparatus insertable into a body of a patient and at least one second subsection of the apparatus, and the first data being for identifying and localizing the at least one first subsection of the apparatus and the at least one second subsection of the apparatus, second processing circuitry configured to train a function based on the input training data and the output training data to determine a trained function, and an output interface to output the trained function.

12. A non-transitory computer-readable medium storing program sections readable in and executable by a computer unit, that, when executed by the computer unit, cause the computer unit to carry out the method of claim 1.

13. The method of claim 2, wherein the at least one second anatomical landmark is in a third subregion in or adjacent to which a position of an end section of the apparatus is expected.

14. The method of claim 2, wherein the apparatus comprises one of:

a central venous catheter insertable into the body of the patient by way of a first vein;

a peripherally inserted central catheter insertable into the body of the patient by way of a vein of an arm of the patient;

an endotracheal probe insertable into the body of the patient by way of a mouth of the patient and a trachea of the patient; or a nasogastric probe insertable into the body of the patient by way of a nose of the patient.

15. The method of claim 2, wherein the at least one first anatomical landmark is at least one of one of:

a trachea of the patient;

a spinal column of the patient; or a long bone of the patient.

16. The method of claim 2, wherein the at least one first subregion is selected as a region in which a number of vessels converge.

17. The method of claim 2, wherein the searching for the at least one first subsection of the apparatus searches for the at least one first subsection of the apparatus based on a first targeted search for a specific type of the apparatus; or the localizing the at least one second subsection of the apparatus localizes the at least one second subsection of the apparatus based on a second targeted search for the specific type of the apparatus.

18. The method of claim 1, wherein the searching is performed in response to detecting the at least one first anatomical landmark in or adjacent to the at least one first subregion.

19. The method of claim 1, wherein the detecting and localizing the at least one second subsection of the apparatus comprises tracing the at least one first subsection of the apparatus into the at least one second subregion or into at least one third subregion adjacent to the at least one second subregion.

* * * * *